United States Patent [19]
Harvie et al.

[11] Patent Number: 5,886,057
[45] Date of Patent: *Mar. 23, 1999

[54] PRODUCTION OF DICARBOXYLIC ACIDS

[75] Inventors: James Lumsden Harvie; Stuart Michael Heppell, both of Cleveland, United Kingdom

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 571,934

[22] PCT Filed: Jun. 29, 1994

[86] PCT No.: PCT/GB94/01410

§ 371 Date: Jan. 4, 1996

§ 102(e) Date: Jan. 4, 1996

[87] PCT Pub. No.: WO95/01953

PCT Pub. Date: Jan. 19, 1995

[30] Foreign Application Priority Data

Jul. 5, 1993 [GB] United Kingdom .................... 9313892
Jul. 5, 1993 [GB] United Kingdom .................... 9313896

[51] Int. Cl.$^6$ ....................................................... C08J 11/04
[52] U.S. Cl. ........................... 521/48; 521/48.5; 521/115; 528/499; 528/495; 528/500; 528/318.1
[58] Field of Search ............................... 521/48, 48.5, 45; 528/499, 500, 502, 308.1, 495, 503

[56] References Cited

U.S. PATENT DOCUMENTS

| | | | |
|---|---|---|---|
| 4,578,502 | 3/1986 | Cudmore | 562/483 |
| 4,578,510 | 3/1986 | Doerr | 562/483 |
| 5,095,145 | 3/1992 | Rosen | 562/483 |
| 5,414,113 | 5/1995 | Broeker et al. | 562/483 |
| 5,426,217 | 6/1995 | Royall et al. | 562/483 |
| 5,532,464 | 7/1996 | Gallagher | 560/78 |

FOREIGN PATENT DOCUMENTS

| | | |
|---|---|---|
| A 0 550 979 | 7/1993 | European Pat. Off. . |
| A 29 38 163 | 4/1981 | Germany . |
| A 2 047 704 | 12/1980 | United Kingdom . |

*Primary Examiner*—James J. Seidleck
*Assistant Examiner*—Olga Asinovsky
*Attorney, Agent, or Firm*—Charles E. Krukiel

[57] ABSTRACT

Dicarboxylic acids or esters thereof are recovered from solid phase polyester materials, such as post-consumer products and factory scrap, by subjecting the polyester to at least two hydrolysis stages in at least the first of which the amount of water used is substantially less than needed to effect total conversion of the polyester to the dicarboxylic acid. Also the diol content is controlled in the course of carrying out the hydrolysis. The hydrolysis reactions may be preceded by reaction of the polyester with a diol, the resulting depolymerisation products then being hydrolysed.

3 Claims, No Drawings

PRODUCTION OF DICARBOXYLIC ACIDS

This invention relates to the production of dicarboxylic acids.

The invention is particularly concerned with the production of such acids by means of the depolymerisation of polyesters, particularly condensation polyesters such as polyalkylene terephthalates and polyalkylene naphthalates, in order to recover dicarboxylic acids.

It is known that terephthalic acid which is suitable for polymerisation with alkylene glycols either directly or after purification may be obtained by the hydrolysis of waste polyalkylene terephthalate. GB-A-2123403 discloses a continuous procedure for obtaining terephthalic acid from PET waste in which the PET waste is heated in water and in which process the presence of decolourising carbon in the water is essential. Additionally, this procedure utilises sufficient water, and is operated at such a temperature, that the terephthalic acid product dissolves in the water as it is produced to form an aqueous solution of terephthalic acid, there being substantially no terephthalic acid in the solid phase, which solution is subsequently filtered to remove the carbon: the terephthalic acid is then crystallised from the filtrate.

It is also known from East German Patent No. 14854 to produce terephthalic acid by hydrolysis of PET. In this case, the teaching also appears to be directed towards producing the terephthalic acid product in solution at the reaction conditions employed. The disclosure refers to filtering the hot reaction solution under pressure using a filter which can trap both coloring and mechanical impurities. The hot solution is thereafter cooled to crystallise the terephthalic acid which is then isolated and dried.

U.S. Pat. No. 5095145 is likewise concerned with effecting depolymerisation of waste PET products by depolymerisation thereof in an aqueous mixture at a temperature within the range 430° to 600° F. to produce an aqueous crude terephthalic acid solution which is thereafter processed further.

U.S. Pat. No. 3257335 discloses a two stage process for depolymerising polyesters, particularly polyethylene terephthalate, to produce low molecular weight terephthalic esters of ethylene glycol in ethylene glycol solutions which can be stored as a liquid at reduced temperatures for extended periods of time without solidification or excessive degradation. The process disclosed comprises dissolving waste polyester in monomer at atmospheric pressure and at a temperature greater than the boiling point of ethylene glycol but less that the boiling point of the mixture, pumping the resulting solution together with fresh ethylene glycol into a tubular reactor at a higher temperature than the dissolver and pressure in excess of the vapor pressure of ethylene glycol at that temperature, recycling part of the reaction product to the dissolver and removing the remainder for storage.

In our prior European Patent Application No. 92 311421.9, there is disclosed a process for the production of terephthalic acid from polyalkylene terephthalate by hydrolysing the terephthalate in such a way that, at the reaction temperature, at least part (preferably a major part) of the terephthalic acid is produced in the solid phase. This provides benefits in terms of the extent of post-reaction crystallisation necessary to recover the terephthalic acid and the extent of water removal necessary to effect recovery of glycol produced in the reaction. The hydrolysis may be carried out in two stages and glycol may be present in the reaction mixture so as to increase the proportion of glycol present relative to water thereby simplifying the recovery of glycol following the reaction.

The present invention seeks to provide an improved process for the depolymerisation of polyesters.

According to the present invention there is provided a process for effecting depolymerisation of polyesters in order to recover the constituent dicarboxylic acid and diol therefrom, including the steps of:

(a) subjecting a polyester, or a treated polyester as herein specified, to a first hydrolysis reaction in such a way that the polyester (or treated polyester) is only partially converted to the constituent diol and the dicarboxylic acid;

(b) separating from the mixture formed in step (a) at least part of the diol present in step (a); and (c) subjecting the mixture remaining after step (b) to at least one further hydrolysis reaction.

As referred to herein, "a pre-treated polyester" refers to a solid phase polyester which, prior to said first stage hydrolysis, has been treated to produce a liquid phase medium which contains primarily low molecular weight depolymerisation products (herein referred to as oligomers) and may contain some higher molecular weight depolymerisation products (in excess of 20 repeat units) and possibly some unreacted polyester.

The invention has application for example to polyesters such as polyalkylene terephthalates in which the dicarboxylic acid comprises terephthalic acid and polyalkylene naphthalates in which the dicarboxylic acid or ester comprises naphthylene 2,6 dicarboxylic acid.

Because the hydrolysis of polyester is an equilibrium process, it is necessary to have a large excess of water over diol in the final reaction mixture to obtain high yields of dicarboxylic acid and diols. Removing even a small amount of diol will thus reduce the required amount of water by a much greater amount. By carrying out the hydrolysis in more than one stage and removing the diol as in step (b) prior to the or each following hydrolysis stage, the invention makes it possible to use relatively high polyester (or treated polyester) loadings relative to the total amount of water used in the process while still obtaining high conversion of polyester to acid and glycol. This in turn results in lesser amounts of effluent requiring treatment prior to disposal, less distillation to recover the diol and reduced operating costs.

The diol present in any hydrolysis reaction will be present in either or both of two forms, free diol (normally dissolved in the aqueous phase) and unhydrolysed diol reacted with the diacid and present in the oligomers or polyester material. It has surprisingly been found that the use of an intermediate hydrolysis step will liberate a significant portion of the diol present in oligomers without the need for large quantities of water. Once liberated, the free diol may be removed more easily.

Typically the process is carried out in two hydrolysis reaction stages. However, it may be carried out in three or even more hydrolysis reaction stages. Preferably in all but the final stage between 10 and 99% (more preferably between 50 and 90%) of the diol which is combined at each such stage with dicarboxylic acid species is liberated. In the final stage preferably at least 90%, more preferably more than 95% and especially more than 99%, of the remaining bound diol is liberated.

It is to be understood that the references to hydrolysis reaction stages herein are not limited to each hydrolysis reaction being carried out separately or in separate reactors. The invention includes within its scope, the carrying out of one hydrolysis reaction concurrently with, ie in the same reactor as, a preceding hydrolysis reaction. For instance, in the case of polyester or treated polyester material which has undergone a first stage hydrolysis, the product of the reaction (following separation therefrom of at least part of the diol present in the first stage hydrolysis reaction) may be recycled at least in part and combined with a "fresh" incoming (unhydrolysed) polyester/treated polyester in the same reactor and the combined materials subjected to hydrolysis. Thus, in this instance, the hydrolysis reaction performed will constitute a second stage hydrolysis reaction for the recycled material and a first stage hydrolysis reaction for the "fresh" incoming material. More generally, where the process involves more than one hydrolysis reaction stage, it will be appreciated that material at different stages of hydrolysis (including material which has yet to be subjected to a first stage hydrolysis) may be hydrolysed in the same reactor concurrently so that, while some material is undergoing its nth hydrolysis reaction stage, other material is undergoing its (n+m)th hydrolysis reaction stage, where n is an integer equal to one or more and m is an integer usually equal to one. Moreover, the various stages of hydrolysis may be carried out either continuously or in batchwise fashion, ie material feed to each hydrolysis being effected continuously or batchwise.

In practice, the first hydrolysis reaction stage is carried out using an amount of aqueous medium which is less than would otherwise be necessary to effect substantially total conversion of the polyester to the polycarboxylic acid.

Preferably said first stage hydrolysis reaction is preceded by treatment of the polyester with a diol to convert it from a solid phase form to said liquid phase medium.

The liquid phase medium following the reaction of the polyester with the diol will also often contain residual diol, particularly where an excess of the diol is used in the reaction.

The hydrolysis reaction generally requires elevated pressure which gives rise to problems, especially in continuous processes, from the standpoint of introducing the solid phase polyester into a hydrolysis reactor under elevated pressure and temperature conditions since solid phase polyester (eg post-consumer and factory scrap) is commonly in a form which is not readily amenable to slurrying and pumping. Also, solid phase often has a relatively low bulk density and the amount of aqueous medium required to totally immerse the polyester is significantly greater than that needed on a weight for weight basis to treat that amount of polyester. By preceding the first stage hydrolysis with reaction of the solid phase polyester with a diol in order to produce said liquid phase medium, the problem of introducing a low bulk density solid phase reactant at atmospheric pressure into elevated pressure conditions is obviated since it is a relatively simple matter to pump a liquid phase medium into a reactor operating under high pressure conditions. Also, the amount of water can be substantially reduced compared with that required to totally immerse low bulk density solid phase polyester. Because diols are much less volatile than water, the reaction of the solid phase polyester with the diol can be carried out at least initially at much lower pressure, eg atmospheric pressure, than is necessary for the first stage hydrolysis reaction.

Another advantage stemming from the preceding reaction with the diol is that the solid phase polyester can be fed substantially continuously into that reaction whereas continuous feed of solid phase polyester directly into a hydrolysis reactor operating under elevated temperature and pressure conditions is technically difficult.

A further advantage conferred by the preceding reaction with the diol, as opposed to carrying out the hydrolysis of solid phase polyester directly, is that various treatments of the resulting liquid phase medium can be carried out prior to carrying out the first stage hydrolysis reaction. In particular, it becomes feasible to subject the liquid phase medium to a separation process, eg filtration, to remove undesirable insoluble particulate impurities, such as aluminum, paper, polystyrene, polyolefines, PVC, commonly present in washed, scrap/post-consumer polyesters. Also, by suitable management of the liquid phase medium, extraction of impurities by means of contact with for instance activated carbon (eg for decolourising the liquid phase medium) or an ion exchange resin may be effected in order to remove contaminants such as chloride or ionic catalyst residues present in the liquefied polyester.

Typically, the reaction of the solid phase polyester with the diol will be carried out at elevated temperature in excess of temperatures at which use of ion exchange resins can normally be entertained; thus, for instance, prior to extraction of contaminants using means such as an ion exchange resin, the liquid phase medium may be cooled to a temperature within a range allowing the use of such extraction means. Water or other suitable polar solvent may be added to the liquid phase medium to assist in solubilising the oligomers at lower temperatures and to assist in ionising impurities to facilitate removal of soluble impurities.

The reaction of the solid phase polyester with the diol may be carried out in two stages, a first low pressure stage in which the reaction with the diol serves to produce said lower molecular weight polyester depolymerisation products and a second higher pressure stage in which the reaction with the diol proceeds further in order to produce even lower molecular weight depolymerisation products. The second stage may involve the introduction of additional diol (which is preferably the same as that used in the first stage). The second stage confers the advantage that the production of even lower molecular weight oligomers permits the liquid phase to be cooled without solidifying to temperatures lower than is possible with longer chain polyester depolymerisation products. It is therefore more feasible to cool the liquid phase medium to within a temperature range compatible with the use of ion exchange resins. Cooling may also be desirable where other filtration/removal techniques, eg activated carbon, semi-permeable membranes, etc, are used.

A further advantage of being able to cool to relatively low temperature without solidification is that the liquid product can be stored as such without degrading significantly.

The first stage of the polyester/diol reaction is conveniently carried out in a continuous fashion with solid phase polyester being introduced to the reaction concurrently with removal of said liquid phase medium. Thus, in steady state operation of the process, liquid phase medium may be continuously withdrawn from the first stage of the reaction and may be pumped continuously into the higher pressure second stage of the polyester/diol reaction.

Advantageously, particularly in terms of aiding eventual separation and recovery thereof, the diol used in the first stage, and where the context admits in each stage, of the polyester/diol reaction is the same as the diol which is derived from the subsequent hydrolysis reaction polyester. For instance, in the case where the starting polyester is constituted by polyethylene terephthalate, the alklene diol used in the polyester/diol reaction (whether carried out in a single or multiple stages) is preferably monoethylene glycol. In some instances, the polyester/diol reaction may be carried out using a mixture of different alkylene diols of which one will preferably be the same as that derived from the polyester in the subsequent hydrolysis reaction.

Some polyesters are produced by the reaction of a polycarboxylic acid with a mixture of diols. Where the polyester to be processed in accordance with the invention is of this type, the diol used in the polyester/diol reaction is preferably the same as the diol which formed the major component of the diol mixture originally used in the production of the polyester.

Preferably in at least the first stage hydrolysis, the polyester/treated polyester content relative to the water content of the aqueous medium and the reaction conditions are such that, were 90% of the theoretical TA based on the polyester/treated polyester initially present to be converted to free dicarboxylic acid, then the solubility limit of the dicarboxylic acid would be exceeded and part of the acid would precipitate under the reaction conditions.

Stated more specifically, preferably at least one of the hydrolysis reaction stages (usually at least the first hydrolysis reaction stage) is operated with a polyester or treated polyester loading (relative to the aqueous phase used in the reaction) together with an aqueous phase composition such that one or both of the following conditions are met:

(a) the quantity of liquor is insufficient, under the reaction conditions prevailing during hydrolysis, to prevent the dicarboxylic acid produced exceeding its solubility limit in the liquor remaining following the hydrolysis reaction; and (b) the conversion of polyester or treated polyester to the acid and glycol is less than 90% (defined in terms of the % of the total acid available for hydrolysis which is actually produced as dicarboxylic acid).

Usually in a hydrolysis reaction stage where the total yield of free dicarboxylic acid is in excess of 40% based on the total amount of dicarboxylic acid species fed to that stage, at least 20% (more preferably at least 30% and especially at least 50%) of the free dicarboxylic acid is produced in the solid phase under the reaction conditions.

Often the penultimate hydrolysis reaction stage is carried out in such a way that, under the prevailing reaction conditions, at least 20% (more preferably at least 50%, especially at least 70%) of the dicarboxylic acid is produced in the solid phase.

Also the final hydrolysis reaction stage is preferably carried out in such a way that, under the prevailing reaction conditions, at least a major part (more preferably at least 70%, and most preferably at least 80%, even as much as 90% or more) of the dicarboxylic acid is produced in the solid phase.

This can be achieved by employing comparatively low reaction temperature for the hydrolysis (certainly less than 300° C., typically in the range 190° to 240° C. and preferably about 200° to about 220° C.) and by using small quantities of water to secure high conversion to dicarboxylic acid. Hydrolysis at temperatures lower than 190° C. may be employed if desired; however in order to secure a dicarboxylic acid yield similar to that obtained at higher temperatures, the reaction time must be increased significantly.

A number of advantages may be secured by effecting the final hydrolysis reaction stage in such a way as to produce a substantial part of the dicarboxylic acid in the solid phase rather than being completely dissolved in the reaction medium. Thus, less recrystallisation is necessary to recover the dicarboxylic acid from the reaction medium as compared with the processes of the prior art.

Also, by ensuring that at least part of the dicarboxylic acid is produced in the solid phase during the course of the final hydrolysis reaction, the reaction equilibrium can be shifted in the desired direction thereby enhancing recovery of the dicarboxylic acid.

The solid phase polyester to be treated in accordance with the process of the invention may be in any suitable form although it is preferred that the polyester is in the form of particles such as granules, powder or flakes, derived by the comminution or other mechanical breakdown of manufactured articles consisting of or containing polyester. For instance, in the case of polyethylene terephthalate (PET), bottles provide a major source of PET suitable for recycling to produce terephthalic acid although it may be desirable to separate the PET from any other plastics materials contained in the bottles such as polyvinylchloride (PVC) prior to hydrolysis. Other sources of PET include fibers and film.

Although it is preferred to comminute polyester products such as bottles into particles, flakes or other finely divided form we do not exclude the possibility of using the process of the invention to treat finished polyester products in order to recover the dicarboxylic acid.

The hydrolysis reaction stages are preferably carried out using demineralised water as the aqueous medium thus reducing the possibility of competing reactions reducing the yield of terephthalic acid.

A further aspect of the present invention is concerned with effecting hydrolysis reaction in all but the final stage hydrolysis reaction in such a way as to simplify removal of the diol produced from intermediate reaction products.

Thus, according to a further aspect of the invention there is provided a process for effecting depolymerisation of polyesters in order to recover a dicarboxylic acid and diol therefrom, including the steps of:

(i) subjecting a polyester, or a treated polyester as herein specified, to a first stage hydrolysis reaction at elevated temperature to convert at least the major proportion of the polyester (or treated polyester) to the dicarboxylic acid and intermediate reaction products of the acid with the diol, the reaction being carried out in such a way that, after precipitating at least a major proportion (and preferably substantially all) of the dissolved intermediate reaction products, the resulting reaction mixture is capable of separating into two distinct phases, namely a supernatant liquid phase substantially comprising water and said diol, and a solid phase comprising said intermediate reaction products and dicarboxylic acid (if present);

(ii) causing or allowing separation of the resulting reaction mixture into said liquid and solid phases and removing at least part of the supernatant liquid phase from the reaction mixture; and (iii) subjecting the mixture remaining after step (ii) to at least one further stage of hydrolysis.

It will be appreciated that the references to hydrolysis reaction stages as used in the preceding paragraph are to be construed in the manner previously referred to. Thus, for example, the further stage of hydrolysis in step (ii) may be effected by combining the mixture remaining after step (ii) to hydrolysis together with material undergoing an earlier stage of hydrolysis and the reactions may be effected either continuously or batchwise.

Usually precipitation of said intermediate reaction products in step (i) is effected by cooling the reaction mixture to a suitable temperature.

At least part or substantially all of the dicarboxylic acid formed in the first stage hydrolysis reaction may be removed prior to precipitation of said intermediate reaction products and/or prior to step (ii). Thus, in step (iii), all or part of the dicarboxylic acid produced in step (i) may be present, or the dicarboxylic acid may be substantially absent as a result of being removed. Dicarboxylic acid so removed may, if desired, be subjected to further hydrolysis separately and/or may be recycled to a different hydrolysis reactor to that used for further hydrolysis of the intermediate depolymerisation products from which dicarboxylic acid is separated.

Preferably substantially all of said supernatant liquid phase is removed from the reaction mixture in step (ii).

Where the process involves more than two hydrolysis reaction stages, at least one of the intermediate hydrolysis reaction stages may be operated in the same way as the first hydrolysis reaction stage (ie. as specified in steps (i) and (ii) above).

In order to produce said reaction mixture capable of separating into distinct liquid and solid phases after precipitation of the intermediate reaction products, the reaction of step (i) is conveniently carried out by limiting the amount of free diol present in the reaction. We have found that control of the diol content limits the formation of components which tend to have a gelling-type action on the resulting reaction mixture. Such components, if present in substantial quantities, lead to the reaction mixture being of a sludge-like character and thereby inhibit separation of the reaction mixture into a distinct supernatant liquid phase and a solid phase. Control of the diol content can be used to limit the amount of such inhibiting components present following each hydrolysis stage (apart from the final stage) thus leading to the production of a reaction mixture which can readily separate into distinct phases.

The diol content of the liquor may be controlled for example by altering the ratio of polyester/treated polyester to water used (if the polyester is not pretreated by reaction with a diol as hereinbefore described); where such pre-treatment is used, control of the diol content can be effected by removing a portion of the excess glycol prior to feeding the pre-treated polyester to the hydrolysis reactor—the amount of diol remaining following such removal will not normally be less than the amount that could have been realised from the starting polyester.

Because of the low solubility of dicarboxylic acids (particularly terephthalic acid) in water, the hydrolysis reaction will usually produce a two phase mixture at the reaction conditions (with the solid being substantially dicarboxylic acid). The dicarboxylic acid may advantageously be separated at a temperature of over 60° C. The liquor under these circumstances may contain a high amount of soluble depolymerisation products. On cooling, the solubility of these products will be reduced and, in the absence of diol control in accordance with this aspect of the invention, may produce a sludge-like mixture in which a clear supernatant forms only very slowly if at all. Separation of the liquor from the 'gelled' solid under these conditions is difficult. The diol control feature of the present invention allows these solid oligomers to be easily separated from the liquor.

Usually step (ii) of the process will involve cooling of the reaction mixture to lower temperatures, typically 60° C. or less, eg. room temperature (ie. of the order of 20° C.) or even lower, in order to cause precipitation of the dissolved intermediate reaction products and separation into the two distinct phases.

By operating all but the final stages of the hydrolysis in this manner, diol present in the reaction mixture can be readily separated from the solid phase components which will largely consist of the dicarboxylic acid or species thereof and which can then be subjected to a further stage or stages of hydrolysis. Thus, the separation can be effected by routine mechanical separation techniques such as decantation or filtration.

The final stage hydrolysis reaction will typically convert substantially all of the depolymerisation products to dicarboxylic acid and diol.

In step (i) of the process, it is advantageous to remove any solid present in the hydrolysis mixture before precipitation of the bulk of the intermediate reaction products as this has been found to increase the volume of supernatant liquor present after precipitaion of the intermediate reaction products. This solid (which is usually substantially entirely dicarboxylic acid) may be blended with the intermediate reaction products after they have been precipitated and separated from the liquor and the mixture hydrolysed in a further hydrolysis stage step (iii). However, as previously indicated, the solid may also with advantage be kept separate, and treated separately to hydrolyse any remaining intermediate reaction products. In this case, the precipitated intermediate reaction products following step (ii) may with advantage be returned to the original hydrolysis reactor and treated with water along with fresh unhydrolysed material. In such a scheme, the recycled material will undergo a subsequent hydrolysis at the same time as the fresh material undergoes its first stage hydrolysis reaction.

For the avoidance of doubt, it is to be understood that the various reaction schemes described throughout may be carried out either on a batch or a continuous basis.

In one embodiment of the invention as applied to the depolymerisation of PET in order to recover terephthalic acid and ethylene glycol (but applicable to other polyesters in order to recover dicarboxylic acid and the associated diol), the solid phase polyester (after being comminuted to a suitable particle size) is subjected to a glycolysis reaction at low pressure (atmospheric or near-atmospheric) but elevated temperature sufficient to produce a liquid phase medium containing the glycol and polyester derivatives (primarily PET oligomers) resulting from the low pressure glycolysis.

The glycolysis reaction is conveniently carried out at atmospheric pressure (or near atmospheric pressure, ie within several pounds per square inch of atmospheric pressure) in the substantial absence of molecular oxygen. The glycolysis reaction preferably employs the same glycol as that used in the production of the polyester, eg ethylene glycol, and at a temperature in the range 140° to 280° C. (more preferably 180° to 260° C., and most preferably at least 210° C., eg up to 230° C.). Usually the reaction is carried out at a temperature which is more than 10° C. in excess of the boiling point of the diol.

Typically the reaction with the glycol is carried out using a PET:diol ratio of at least 1:1, more preferably at least 1.5:1 and often at least 2:1.

The low pressure glycolysis reaction is preferably carried out on a continuous basis with solid phase PET and ethylene glycol being supplied to the reaction concurrently with removal of liquid phase medium from the reaction and may be carried out at a temperature in excess of the normal boiling point (about 196° C.) of the ethylene glycol used since the oligomers generated during the course of the reaction tend to have high boiling points thereby reducing the liquid vapor pressure and allowing the reaction to proceed without boiling off substantial quantities of the glycol. By carrying out the reaction at an elevated temperature compared with the normal boiling point of the glycol, the reaction may proceed more rapidly.

Liquid phase medium withdrawn from the low pressure glycolysis reaction is conveniently filtered at this stage using some form of mechanical filter to screen out particulates such as aluminum, lumps of PVC, paper etc commonly present in scrap/post-consumer PET. The liquid phase medium may then be optionally treated to remove other impurities, for instance by contact of the medium with activated carbon and/or an ion exchange resin, in which case cooling of the liquid phase medium is effected prior to such contact. Thus, where for example a technique involving contact with a material such as an ion exchange resin is employed, requiring the liquid phase medium to be cooled to a temperature compatible with the material employed in such technique, the liquid phase medium is typically cooled to a temperature within the range 50° to 130° C. (preferably 70° to 100° C.) prior to treatment by such technique. The cooling may be effected either prior to filtration of insoluble impurities (eg aluminum, paper, PVC etc) from the liquid phase medium or subsequent to such filtration.

Optionally the liquid phase medium containing glycol and low molecular weight depolymerisation products is subjected to a second glycolysis reaction at increased pressure (if necessary with added glycol) to enhance the degree of depolymerisation, preferably to form hydroxy ethylene terepthalate compounds of the form:

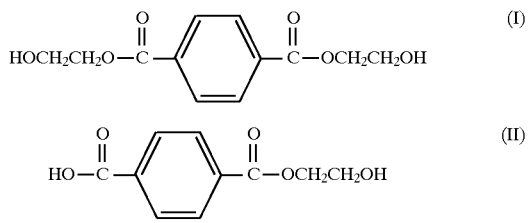

(which may be termed bis-hydroxy ethylene terephthalate (BBET) and mono-hydroxy ethylene terephthalate (MHET) respectively). Usually the diglycol depolymerisation products (such as BBET) will be the predominant components and there may be little if any depolymerisation products with acid groups (such as MHET) present. Acid end groups are usually formed as a consequence of water being introduced into the glycolysis reactor (eg as a result of using damp glycol or PET). The more severe glycolysis reaction may be carried out at a temperature within the range 180° to 260° C. (preferably 210° to 230° C.) and a pressure in the range 1 to 10 bara (preferably 2 to 5 bara).

The liquid phase medium derived from the first glycolysis stage may be pumped continuously from the first stage to the second glycolysis stage.

Where two stages of glycolysis are used, both stages are conveniently carried out in the substantial absence of molecular oxygen. Also, the filtration and other treatment processes may be carried out at any suitable point in the process, eg before or after the second stage. Typically, the filtration of insoluble contaminants may be effected at a point intermediate the two stages by passage of the liquid phase medium through a metal gauze or the like and the extraction of impurities using activated carbon, ion exchange resins or the like may be carried out after the second stage, following cooling and pressure let-down of the liquid phase medium if necessary.

Following glycolysis and optional treatments such as impurity filtration/extraction and glycol reduction, the liquid phase medium may be cooled and collected for storage in a buffer tank or tanks.

Further details of the pre-treatment of the polyester by glycolysis are given in our copending Application of even date (also claiming priority from UK Patent Applications Nos. 9313892.3 and 9313896.4), the disclosure of which is incorporated herein in its entirety by this reference.

Prior to hydrolysis of the liquid phase medium (following glycolysis reaction in one or two stages), the medium is conveniently processed to reduce its glycol content, eg by flashing in a suitable vessel, thereby requiring less water in the subsequent aqueous hydrolysis step to generate any desired number of acid end groups. The glycol content will comprise both glycol added as reactant (in both glycolysis stages where applicable) and that generated in the course of the glycolysis and the reduction process will usually result in removal of a major part of the glycol. The removal of glycol, eg by flashing, is preferably effected, eg at low pressure, to avoid excessive rise in viscosity and repolymerisation of the hydroxy ethylene terephthalate compound (s).

The hydrolysis reaction is carried out in at least two stages and may comprise a substantially neutral aqueous phase hydrolysis, ie substantially in the absence of added acids or alkalis.

In the first stage of the hydrolysis reaction, the treated polyester obtained from the above described two stage glycolysis process is contacted with aqueous medium in a vessel such as an autoclave at a relatively low reaction temperature (certainly less than 300° C., typically in the range 190° to 240° C. and preferably about 200° to about 220° C.). Hydrolysis at temperatures lower than 190° C. may be employed if desired but the reaction time then has to be increased significantly.

The quantity of water added in the first stage is less than that required for total conversion of the polyester/treated polyester to terephthalic acid. Following the first hydrolysis reaction, at least a major part of the liquor (which will contain significant amounts of glycol) is separated from the terephathalic acid and acid/glycol reaction products. If necessary, more water is then added to the remaining material and further hydrolysis is effected under conditions as specified above to yield terephthalic acid as an end product. Alternatively, the second hydrolysis may be an intermediate reaction followed by a further stage or stages of hydrolysis. For instance, the second stage hydrolysis may be carried out using less water than is necessary to achieve substantially total conversion of the material remaining after the first stage hydrolysis to terephthalic acid. In this event, following the second stage hydrolysis, the liquor is again removed and the material yielded by the second stage hydrolysis (comprising terephthalic acid and species thereof) is subjected to a further hydrolysis reaction.

The advantages of this approach are that less water in total is required in order to achieve a given degree of hydrolysis, and the liquor recovered from the first stage has a much higher glycol content which makes glycol recovery easier.

The first hydrolysis stage is desirably carried out in such a way as to produce a reaction mixture which is amenable to separation into two distinct phases following cooling to precipitate any terephthalic acid species. If desired, free dicarboxylic acid may be recovered prior to precipitation of the bulk of the dissolved oligomers but, in this case, it is advantageous not to cool so far as to precipitate the bulk of the dissolved oligomers.

Especially desirable is to control the glycol level so that after cooling to between 70° C. and 200° C. the solid present is at least 50% preferably at least 70% and especially at least 90% terephthalic acid. This solid is normally present in an easily seperable form (a clear supernatant liquid above a rapidly settling solid). After removal of this solid, the residual liquid may be cooled further in order to precipitate the bulk of the dissolved terepthalic species (typically to about 25° C.). It is especially desirable to control the glycol level in the original liquor so that, on cooling, the solid which is precipitated in this stage leaves a clear supernatant. This liquor component of the reaction mixture, being a well-defined supernatant liquid, can be readily removed by decantation or mechanical filtration.

The liquor so removed may, given time, tend to throw a precipitate of further slow crystallising species containing terephthalic acid which may be recovered, for example in a settling tank, and following settling the lower portion of the liquor/solid can be recycled for hydrolysis together with subsequent batches of polyester/treated polyester. The upper portion from the settling tank may be treated in order to effect glycol and water recovery.

One advantage of this method of removing the liquor comprising the liquid phase component of the hydrolysis reaction mixture is that if the hydrolysis reaction is not conducted in such a way as to achieve effective separation of the reaction mixture into two distinct phases, a process such as distillation would be needed to recover the liquor from the hydrolysed solid and, in that event the water will come off first leaving glycol only and while some of the glycol will be removed, the rest will either remain on the solid or will react with the terephthalic acid thereby reversing the hydrolysis reaction.

Another advantage is that the liquor separated from the solid contains any soluble contaminants present in the scrap PET not removed by previous purification steps.

However the liquor is removed, it is likely that it may be recycled by either distillation of the first hydrolysis liquor or storing liquor from the second or third hydrolysis for use as the aqueous phase in a preceding hydrolysis stage. This latter possibility arises since each succeeding stage of hydrolysis will produce a liquor having a lower glycol content (and hence a more water rich liquor) which can be recycled to a preceding hydrolysis stage.

After hydrolysis is complete, the terephthalic acid is recovered by suitable filtration and drying (if required—ie. drying may not be necessary if the recovered terephthalic acid is to be blended with terephthalic acid derived from other sources such as the liquid phase oxidation of p-xylene). Advantageously the recovery of the terephthalic acid includes one or more washing steps, using the same or different wash liquors for each step where multiple washing steps are employed, to remove particular species of organic impurities (for instance to ensure food contact approval), especially water insoluble impurities, to reduce the water content and improve the product color.

The washing step(s), or any one or more of them, may be carried out using heated wash liquor.

Filtration of the terephthalic acid is conveniently carried out by means of a belt filter. Following filtration the terephthalic acid filter cake may be transported on the belt filter through one or more washing stages in which it is washed with a wash liquor or more than one wash liquor, the wash liquor(s) being drawn through the belt filter to leave a washed deposit which may then be dried in any suitable manner. Acetone is a convenient washing liquor since it may serve all of the purposes mentioned above, ie removal of organic species, improvement of product color and drying. The use of acetone as a wash liquor in this manner, ie washing of terephthalic acid particularly terephthalic acid recovered by hydrolysis of polyester or pre-treated polyester as referred to herein, constitutes a further aspect of the invention which may be considered additional to or separate from other aspects of the invention disclosed herein.

The terephthalic acid recovered from the process may be re-used in the production of polyesters, if necessary after the terephthalic acid has been subjected to a purification process such as that conventionally employed in the production of pure terephthalic acid. Thus, for example, the recovered terephthalic acid may be dissolved to form an aqueous solution which is then contacted with hydrogen in the presence of a noble metal catalyst (eg palladium and/or platinum supported on an inert support such as carbon) at a temperature within the range 250° to 350° C. and hydrogen partial pressure of 5 to 25 bara. Alternatively the terephthalic acid may be purified by recrystallisation from solution.

As mentioned previously, it can be advantageous to effect hydrolysis in such a way that a substantial proportion of the terephthalic acid is produced in the solid phase during the course of the reaction. The formation of terephthalic acid in the solid phase during the hydrolysis reaction results in a relatively small particle size and also allows particle size to be controlled at this stage. More specifically, particle formation is preferably controlled in such a way that the particles of solid phase terephthalic acid particles forming during the hydrolysis reaction are of rounded shape, desirably such that at least 90% of the particles of the recovered solid phase terephthalic acid are sufficiently small to pass through a sieve having a grid size 2 mm, preferably 1 mm, more preferably 800 microns, and especially 500 microns square.

Thus, by controlling the particle size during the hydrolysis reaction, it becomes possible to achieve a desired particle size and distribution consistent with the requirements imposed by subsequent processing of the terephthalic acid product, without the necessity for a separate processing vessel (eg crystalliser) for treating the terephthalic acid in order to obtain the desired particle size and distribution. Various ways of controlling particle size can be contemplated such as control of the temperature gradient within the reaction vessel and/or the provision of surfaces which promote formation of the desired particle shape and size. One particularly effective control techique is to effect agitation of the reaction mixture during hydrolysis, for example by means of stirring.

Agitation may be continued after the hydrolysis reaction has been completed and during cooling of the reaction mixture so as to promote crystallisation of terephthalic acid which has remained in solution in the form of rounded particles (as opposed to needle-shaped particles which may be up to 1 cm or above in length as tends to happen if the solution is allowed to cool naturally).

Preferably therefore, the reaction mixture is suitably agitated during heating. By suitably controlling particle size formation from the reaction mixture, for instance by agitation of the reaction mixture, it is possible to secure that at least 90% of terephthalic particles recovered are of rounded shape capable of passing a sieve having a square grid size of 2 mm (more preferably 1 mm and even more preferably 500 microns), as opposed to needle-shaped particles, which is advantageous when the particles are subsequently slurried with alkylene glycol in the course of PET production since particle packing density is of importance in this respect.

It will be understood that, where in the processes disclosed above references are made to terephthalic acid, such processes may also be applied to such other dicarboxylic acids and diols as are used in the production of polyesters.

The invention will now be described further by way of illustration only with reference to the following Examples.

EXAMPLE 1

1000 g of pulverised PET and 2000 g of MEG were introduced into a 4 liter capacity autoclave fabricated from a Hastalloy material and fitted with a nitrogen purge for producing an inert gas atmosphere within the interior of the autoclave. The components were mixed by means of a small turbine stirrer and were heated to 200° C. for 5 hours with 2000 g MEG to produce a liquid phase product. The product was found to have Mn=305, Mw=367. The liquid was passed hot through a 300 micron brass sieve. The liquid was then distilled at atmospheric pressure, the glycol boiling off at up to 200° C. 640 g of glycol was removed in this way so that less water is needed in the subsequent hydrolysis reaction to facilitate easy separation of liquor from precipitated oligomers. At this stage, Mn of the product was found to be 341, indicating that some repolymerisation had occurred.

Following removal of glycol, 1500 ml distilled water was added to the product and the mixture was heated to 203° C. in an inert gas atmosphere for 2 hours. The amount of water used in this stage is significantly less than that required to effect total conversion of the polyester to terephthalic acid.

The reaction mixture was then cooled to 70° C. and was found to form a well-defined two phase system comprising a clear yellow/brown supernatant liquor and a solid phase residue. Substantially all of the supernatant, amounting to 1200 ml of the liquor, was sucked out using a dip pipe fitted with a fibrous felt filter. The resulting damp residue was found to comprise 75% by weight solid of which about 97% by weight was terephthalic acid. Of the supernatant liquor removed, 1000 ml was cooled to room temperature (about 23° C.) and 100 g of solid material was found to have precipitated out. This solid material was readily filtered from the liquor and, on analysis, was found to comprise almost 100% MET.

Following removal of the liquor from the two phase reaction product resulting from the first stage hydrolysis, a second stage hydrolysis was carried out by adding 667 ml of water to the vessel contents (comprising the terephthalic acid-containing solid phase residue), and the mixture was heated to 200° C. for 2 hours in an inert gas atmosphere to complete the hydrolysis. A white powder product was recovered following cooling which was found to comprise approximately 99% terephthalic acid by weight.

Normally, using a single stage hydrolysis without pre-glycolysis, it would be necessary to use about 4 litres of water to obtain a yield of 99% from 1000 g of PET. If pre-glycolysis is used, an amount of water considerably in excess of 4 litres would be needed to secure the same yield. In contrast, it will be seen that the process of the invention as illustrated by Example 1 can be carried using a substantially reduced amount of water.

EXAMPLE 2

300 g glycol was heated with 700 g PET flake under an inert gas atmosphere in an insulated glass vessel fitted with a nitrogen purge, a thermocouple and a condenser. The vessel was open to atmosphere and was vapor-jacketed, the vapor being supplied by boiling dodecanol (bp. 260° C.). The liquid finally reached 226° C. and was held at this temperature for 4 hours. After this time Mn and Mw were found to be 431 and 583 respectively. The liquid was drained out of the vessel via a tap in the base, the tap being provided with a filter in the form of a plug of glass wool. Because only a small amount of glycol had been added to the PET there was no need to remove the glycol prior to hydrolysis.

883 g of the glycolysed material was transferred to the autoclave of Example 1 and 871 g of distilled water were added. The mixture was heated with stirring for 2.5 hours at 206° C. The amount of water employed constituted about ⅕th of that necessary to effect total conversion of the polyester to terephthalic acid. The stirrer rate was 400 rpm (small turbine stirrer). After 2.5 hours, the pot contents were cooled to 70° C. The product was a white powder with a clear yellow/brown supernatant liquor. The supernatant layer (about 1000 ml) of liquor was removed by suction through a dip pipe fitted with a fibrous felt filter. The dried solid was found to comprise 95.2% terephthallic acid by weight.

A further 1240 g distilled water was then added to the remaining solid in the vessel and the mixture was reheated to 200° C. for 2 hours. The product was filtered hot and rinsed in acetone and dried. A white powder was recovered containing 98.3% by weight terephthalic acid, less than 1.5 ppm of each of Na, Mn and Co and 4.7 ppm Sb.

EXAMPLE 3

A sample of post-consumer PET was glycolysed for 2 hours at 260° C. using two parts by weight glycol to one part PET. The conductance of a cell containing the material at 80° C. was 2.0 $\mu$S. The material was passed (at 80° C.) through a column containing a bed of cation ion exchange resin followed by a bed of anion ion exchange resin. The conductance of a cell containing the material produced from the ion exchange resins at 80° C. was 0.2 $\mu$S, demonstrating that a significant proportion of the free ions had been removed. Elemental analysis showed the starting material and treated material to contain the elements at the levels given below:

| Element | Starting Material | Treated Material |
| --- | --- | --- |
| Sb | 45 ppm | 1.5 ppm |
| Cl | 79 ppm | 11 ppm |

This Example illustrates the advantage obtainable by liquefying the PET polyester prior to hydrolysis, ie the cooled liquid phase medium can be treated using ion exchange resins to remove certain impurities.

EXAMPLE 4

A sample of PET which had been deliberately contaminated with benzophenone was hydrolysed using the process described in Example 2. After contamination, the PET contained 1.64% benzophenone by weight. The resulting terephthalic acid produced by the hydrolysis contained approximately 0.11% benzophenone by weight. 20 g the terephthalic acid product was treated by Soxhlet extraction using 200 g of acetone. The acetone obtained following the extraction procedure was found to contain 0.014% benzophenone by weight. No benzophenone could be detected in the terephthalic acid following treatment thereof with acetone indicating that any residual benzophenone content was less than 100 ppm.

It will be appreciated that, whilst the invention has been described hereinbefore with reference to the processing of PET to recover terephthalic acid and glycol, similar process steps may be employed in the case of other condensation polyesters such as polyethylene naphthalate.

We claim:

1. A process for depolymerizing a scrap or post-consumer solid condensation polyester selected from polyalkylene naphthalate and polyalkylene terephthalate to recover the constituent dicarboxylic acid and diol therefrom which comprises:

(a) comminuting the solid polyester;
   (b) reacting the comminuted polyester with a diol in the absence of water at a polyester:diol ratio of at least 1:1 by weight and at a temperature within the range of 140° to 280° C. to produce a liquid phase medium;
   (c) removing diol from the liquid phase medium;
   (d) subjecting said liquid phase medium from step (c) to a first hydrolysis reaction which comprises contacting said liquid phase medium with water at a temperature in the range of from 190° to 240° C. whereby a first portion of the constituent dicarboxylic acid present in the liquid phase medium precipitates;
   (e) separating from the reaction medium formed in step (d) at least part of the diol present therein and optionally removing from the reaction medium at least some of said first portion of constituent dicarboxylic acid precipitate;
   (f) subjecting the reaction medium remaining after step (e) to at least one further hydrolysis reaction which comprises contacting said reaction medium with water at a temperature in the range of from 190° to 240° C. whereby at least a second portion of the constituent dicarboxylic acid present in the liquid phase medium from step (b) precipitates; and
   (g) optionally washing and filtering the precipitate from steps (d) and (f) to recover the constituent dicarboxylic acid.

2. The process as claimed in claim 1 in which the reaction in step (b) is carried out at a temperature which is in excess of 10° C. above the boiling point of the constituent diol.

3. The process as claimed in claim 1 in which reacting the comminuted polyester with a diol in step (b) comprises (i) reacting the comminuted polyester with a diol at atmospheric pressure in a first low pressure stage, and then (ii) reacting the mixture resulting from step (i) with a diol at a second high pressure stage in the optional presence of additional diol than was present in step (i), with the proviso that the diol used in steps (i) and (ii) is the same diol used originally as a major component in the production of the polyester and steps (i) and (ii) are carried out in the substantial absence of molecular oxygen.

* * * * *